US00RE37462B1

(19) United States
(12) Reissued Patent
Rosenblum et al.

(10) Patent Number: US RE37,462 E
(45) Date of Reissued Patent: Dec. 4, 2001

(54) PROTEIN SEQUENCE OF THE PLANT TOXIN GELONIN

(75) Inventors: Michael Rosenblum, Sugar Land, TX (US); William J. Kohr, San Mateo, CA (US); Bharat Aggarwal, Houston, TX (US)

(73) Assignee: The Research Development Foundation, Carson City, NV (US)

(21) Appl. No.: 09/316,071

(22) Filed: May 20, 1999

Related U.S. Patent Documents

Reissue of:
(64) Patent No.: 5,631,348
Issued: May 20, 1997
Appl. No.: 08/254,662
Filed: Jun. 6, 1994

U.S. Applications:

(63) Continuation of application No. 08/119,899, filed on Sep. 10, 1993, now abandoned, which is a continuation of application No. 07/908,959, filed on Jul. 6, 1992, now abandoned, which is a continuation of application No. 07/567,220, filed on Aug. 14, 1990, now abandoned.

(51) Int. Cl.[7] ..... C07K 14/415
(52) U.S. Cl. ..... 530/370; 536/23.6
(58) Field of Search ..... 435/440, 252.3, 435/252.33; 536/23.6; 530/370

(56) References Cited

U.S. PATENT DOCUMENTS

| | | | |
|---|---|---|---|
| 4,446,240 | 5/1984 | Nerenberg | 436/542 |
| 4,810,648 | 3/1989 | Stalker | 435/191 |
| 4,888,415 | 12/1989 | Lambert et al. | 530/390 |
| 4,921,802 | 5/1990 | Hall et al. | 435/440 |
| 5,631,348 | 5/1997 | Rosenblum et al. | 530/370 |

FOREIGN PATENT DOCUMENTS

WO 89/04839 6/1989 (WO) .

OTHER PUBLICATIONS

Dickerson, Jr. and Lou, "Micro–quantitation of lens myo–inositol by anion exchange chromatography," *Curr. Eye Res.*, 9(2):201–205, 1990.

Montanaro et al., "A metalloproteinase associated with gelonin, a ribosome inactivating protein," *Ital. J. Biochem*, pp. 1–10, 1985.

Toy, "The Inerferons", *Clin. Exp. Immunol.*, 54:1–13, 1983.

Stirpe et al., "Gelonin, a new inhibitor of protein synthesis, nontoxic to intact cells," *J. Biol. Chem.*, 255 (14):6947–6953, 1980.

Young and Davis, "Yeast RNA polymerase II genes: Isolation with antibody probes," *Science*, 222:778–782, 1983.

Sivam et al., "Immunotoxins to a human melanoma–associated antigen: Comparison of gelonin with ricin and other A chain conjugates," *Cancer Res.*, 47:3169–3173, 1987.

Falasca et al., "Properties of the ribosome–inactivating proteins gelonin, *momordica charantia* inhibitor, and dianthins," *Biochem. J.*, 207:505–509, 1982.

Jacobs et al., "Isolation and characterization of genomic and cDNA clones of human erythropoietin," *Nature*, 313:806–810, 1985.

Watanabe et al., "Selection of chromatographic protein purification operations based on physicochemical properties," *Annals New York Academy of Science*, 348–359, 1994.

Roselli et al., "Comparative biodistributions of yttrium– and indium–labeled monoclonal antibody B72.3 in athymic mice bearing human colon carcinoma xenografts," *J. Nucl. Med.*, 30:672–682, 1989.

Lambert et al., "Immunotoxins containing single–chain ribosome–inactivating proteins, ABSTRACt," *Cancer Treat. Res.*, 37:175–209, 1988.

Ronneberger, "Toxicological testing of monoclonal antibodies," ABSTRACT, *Dev. Biol. Stand.*, 71:185–90, 1990.

Edwards et al., "A simple and rapid method method for the preparation of plant genomic DNA for PCR analysis," *Nucleic Acids Research*, 19(6):1349, 1991.

Dunbar, "Purification of proteins from polyacrylamide gels," In: Two–dimensional electrophoresis and immunological techniques, Plenum Press, New York and London, pp. 32–34, 1987.

Sperti et al., "Interaction of gelonin with zinc." *Ital. J. Biochem.*, 35(4):266–271, 1986.

Montecucchi et al., "N–terminal sequence of some ribosome–inactivating proteins," *Int. J. Peptide Protein Res.*, 33:263–267, 1989.

Young and Davis, "Efficient isolation of genes by using antibody probes," *Proc. Natl. Acad. Sci. USA*, 80:1194–1198, 1983.

Collins et al., "Primary amino acid sequence of α–trichosanthin and molecular models for abrin a–chain and α–trichosanthin," *J. Biol. Chem.*, 265(15):8665–8669, 1990.

Pastan et al., "Immunotoxins," *Cell*, 47:641–646, 1986.

Descotes et al., "The immunological activity of plant toxins used in the preparation of immunotoxins–II. The immunodepressive activity of gelonin," *Int. J. Immunopharmac.*, 7(4):455–463, 1985.

Srinivasan et al., "Chemical modification studies of gelonin, "*FEBS*, 192(1):113–118, 1985.

Lambert et al., "Purified immunotoxins that are reactive with human lymphoid cells," *J. Biol.Chem.*, 260(22):12035–12041, 1985.

(List continued on next page.)

*Primary Examiner*—James Ketter
(74) *Attorney, Agent, or Firm*—Fulbright & Jaworski L.L.P.

(57) ABSTRACT

This invention relates to substantially purified gelonin, toxic fragments thereof, the DNA sequences encoding gelonin and use of the DNA for producing, by recombinant technology, gelonin, toxic fragments thereof and fusion proteins. More specifically, the invention relates to the primary amino acid sequence of gelonin, and of the DNA encoding said gelonin and the production of synthetic gelonin and toxic fragments thereof.

18 Claims, 13 Drawing Sheets

OTHER PUBLICATIONS

Knowles and Thorpe, "Purification of immunotoxins containing ricin A–chain and abrin A–chain using blue sepharose CL–6B," *Analytical Biochem.*, 160:440–443, 1987.

Myers and Villemez, "Specific chemical cleavage of diphtheria toxin with hydroxylamine," *The J. of Biol. Chem.*, 263(32):17122–17127, 1988.

Kusui et al., "cDNA cloning and expression of *bauhinia purpurea* lectin," *J. Biochem.*, 109:899–903, 1991.

Hertler and Frankel, "Immunotoxins: a clinical review of their use in the treatment of malignancies," *J. Clin. Oncology*, 7(12):1932–1942, 1989.

Spooner and Lord, "Expression of antibody–ricin A chain fusions in mammalian cells," In: Applications in clinical oncology, Agamemnon Epenetos (Ed.), pp. 65–77, 1994.

Maxwell et al., "Regulated expression of a diphtheria toxin A–chain gene transfected into human cells: possible strategy for inducing cancer call suicide," *Cancer Research*, 46(9):4660–4664, 1986.

Harrison et al., "Inhibition of human immunodeficiency virus–1 production resulting from transduction with a retrovirus containing an hiv–regulated diphtheria toxin A chain gene," *Human Gene Therapy*, 3:461–469, 1992.

Ogata et al., "Cell–mediated cleavage of pseudomonas exotoxin between $Arg^{279}$ and $Gly^{280}$ generates the enzymatically active fragment which translocates to the cytosol," *J. Biolog. Chem.*, 267(35):25396–25401, 1992.

Debinski and Pastan, "Monovalent immunotoxin containing truncated form of pseudomonas exotoxin as potent antitumor agent," *Cancer Res.*, 52:5379–5385, 1992.

Palmiter et al., "Cell lineage ablation in transgenic mice by cell–specific expression of a toxin gene," *Cell*, 50:435–443, 1987.

Zamboni et al., "High–pressure–liquid–chromatographic and fluorimetric methods for the determination of adenine released from ribosomes by ricin and gelonin", *Biochem. J.*, 259:639–643, 1989.

Theuer et al., "A recombinant form of pseudomonas exotoxin directed at epidermal growth factor receptor that is cytotoxic without requiring proteolytic processing," *Jour, Biological C.*, 267(24):16872–16877, 1992.

Benoit et al., *Curr. Eye Res.*, vol. 9 Suppl., 1990, pp. 201–205.

```
  1  GGNYTNGAYA CNGTNWSNTT YWSNACNAAR GGNGCNACNT AYATHACNTA
     CCNRANCTRT GNCANWSNAA RWSNTGNTTY CCNCGNTGNA TRTADTGNAT
     GlyLeuAspT hrValSerPh eSerThrLys GlyAlaThrT yrIleThrTy

                                                   ecoRI
 51  YGTNAAYTTY YTNAAYGARY TNMGNGTNAA RYTNAARCCN GARGGNAAYW
     RCANTTRAAR RANTTRCTYR ANKCNCANTT YRANTTYGGN CTYCCNTTRW
     rValAsnPhe LeuAsnGluL euArgValLy sLeuLysPro GluGlyAsnSer

            ecoRI
101  SNCAYGGNAT HCCNYTNYTN WSNAARGGNG AYGAYCCNGG NAARTGYTTY
     SNGTRCCNTA DGGNRANRAN WSNTTYCCNC TRCTRGGNCC NTTYACRAAR
       HisGlyIl eProLeuLeu SerLysGlyA spAspProGl yLysCysPhe

151  GTNYTNGTNG CNYTNWSNAA YGAYAAYGGN CARYTNGCNG ARATHGCNAT
     CANRANCANC GNRANWSNTT RCTRTTRCCN GTYRANCGNC TYTADCGNTA
     ValLeuValA laLeuSerAs nAspAsnGly GlnLeuAlaG luIleAlaIle

201  HGAYGTNACN WSNGTNTAYG TNGTNGGNTA YCARGTNMGN AAYMGNWSNT
     DCTRCANTGN WSNCANATRC ANCANCCNAT RGTYCANKCN TTRKCNWSNA
      AspValThr SerValTyrV alValGlyTy rGlnValArg AsnArgSerT

251  AYTTYTTYAA RGAYGCNCCN GAYGCNGCNT AYGARGGNYT NTTYAARAAY
     TRAARAARTT YCTRCGNGGN CTRCGNCGNA TRCTYCCNRA NAARTTYTTR
     yrPhePheLy sAspAlaPro AspAlaAlaT yrGluGlyLe uPheLysAsn

301  ACNATHAARA AYCCNYTNYT NTTYGGNGGN AARACNMGNY TNCAYTTYGG
     TGNTADTTYT TRGGNRANRA NAARCCNCCN TTYTGNKCNR ANGTRAARCC
     ThrIleLysA SnProLeuLe uPheGlyGly LysThrArgL euHisPheGl

351  NGGNWSNTAY CCNWSNYTNG ARGGNGARAA RGCNTAYMGN GARACNACNG
     NCCNWSNATR GGNWSNRANC TYCCNCTYTT YCGNATRKCN CTYTGNTGNC
     yGlySerTyr ProSerLeuG luGlyGluLy sAlaTyrArg GluThrThrAsp

401  AYYTNGGNAT HGARCCNYTN MGNATHGGNA THAARAARYT NGAYGARAAY
     TRRANCCNTA DCTYGGNRAN KCNTADCCNT ADTTYTTYRA NCTRCTYTTR
       LeuGlyIl eGluProLeu ArgIleGlyI leLysLysLe uAspGluAsn

451  GCNATHGAYA AYTAYAARCC NACNGARATH GCNWSNWSNY TNYTNGTNGT
     CGNTADCTRT TRATRTTYGG NTGNCTYTAD CGNWSNWSNR ANRANCANCA
     AlaIleAspA snTyrLysPr oThrGluIle AlaSerSerL euLeuValVal

501  NATHCARATG GTNWSNGARG CNGCNMGNTT YACNTTYATH GARAAYCARA
     NTADGTYTAC CANWSNCTYC GNCGNKCNAA RTGNAARTAD CTYTTRGTYT
      IleGlnMet ValSerGluA laAlaArgPh eThrPheIle GluAsnGlnI

551  THMGNAAYAA YTTYCARCAR MGNATHMGNC CNGCNAAYAA YACNATHWSN
     ADKCNTTRTT RAARGTYGTY KCNTADKCNG GNCGNTTRTT RTGNTADWSN
     IeArgAsnAs nPheGlnGln ArgIleArgP roAlaAsnAs nThrIleSer

601  YTNGARAAYA ARTGGGGNAA RYTNWSNTTY CARATHMGNA CNWSNGGNGC
     RANCTYTTRT TYACCCCNTT YRANWSNAAR GTYTADKCNT GNWSNCCNCG
     LeuGluAsnL ysTrpGlyLy sLeuSerPhe GlnIleArgT hrSerGlyAl
```

FIG. 2A

```
651  NAAYGGNATG TTYWSNGARG CNGTNGARYT NGARMGNGCN AAYGGNAARA
     NTTRCCNTAC AARWSNCTYC GNCANCTYRA NCTYKCNCGN TTRCCNTTYT
     aAsnGlyMet PheSerGluA laValGluLe uGluArgAla AsnGlyLysLys

701  ARTAYTAYGT NACNGCNGTN GAYCARGTNA ARCCNAARAT HGCNYTNYTN
     TYATRATRCA NTGNCGNCAN CTRGTYCANT TYGGNTTYTA DCGNRANRAN
       TyrTyrVa lThrAlaVal AspGlnValL ysProLysIl eAlaLeuLeu

751  AARTTYGTNG AYAARGAYCC NGAR
     TTYAARCANC TRTTYCTRGG NCTY
     LysPheValA spLysAspPr oGlu

>length:  774

ecoRI(GAATTC)        96 107 572
not found
```

| WHEREIN: | | | |
|---|---|---|---|
| | R = A,G | K = G,T | N = any |
| | Y = C,T | M = A,C | S = C,G |
| | B = C,G,T | V = A,C,G | : = unknown |
| | D = A,G,T | W = A,T | - = ignored |
| | H = A,C,T | X = unknown | |

FIG. 2B

PROTEIN SEQUENCE OF THE PLANT TOXIN GELONIN

Matter enclosed in heavy brackets [ ] appears in the original patent but forms no part of this reissue specification; matter printed in italics indicates the additions made by reissue.

This is a *reissue of Ser No. 08/254,662 filed Jun. 6, 1994, now U.S. Pat. No. 5,631,348 which is a* continuation of application Ser. No. 08/119,899 filed on Sep. 10, 1993, now abandoned, which is a continuation of U.S. Ser. No. 07/908,959 filed Jul. 6, 1992, abandoned, which is a continuation of U.S. Ser. No. 07/567,220, filed Aug. 14, 1990, now abandoned.

TECHNICAL FIELD

This invention relates to substantially purified gelonin, toxic fragments thereof, the DNA sequences encoding gelonin and use of the DNA for producing, by recombinant technology, gelonin, toxic fragments thereof and fusion proteins. More specifically, the invention relates to the primary amino acid sequence of gelonin, and of the DNA encoding said gelonin and the production of synthetic gelonin and toxic fragments thereof.

BACKGROUND ART

A major challenge for the design of a drug for treatment of any disease is specificity and efficacy. Various drugs available for the treatment of cancer suffer from problems of this nature. The concept of targeting toxic drugs selectively to certain tumors has been a subject of intense research in the last few years (Thorpe (1985) Biol Clin Applications 84:475–512; Moller ed. (1982) Immun. Rev. 62:1–215). Recently both monoclonal and polyclonal antibodies, lectins, lymphokines and hormones which recognize specific determinants on the surface of the tumor cell have been used as carriers to deliver toxic agents into the cell, where the latter can exert their cytotoxic potential (Blattler, et al. (1985) Biochemistry 24:1517–1524; Frankel, et al. (1985) J. Biol. Res. Modif. 4:437–446; Reimann, et al. (1988) J. Clin. Invest. 82:129–138; Schwartz and Vale (1988) Endocrinology 122:1695–1700; Scott, et al. (1987) J Natl. Cancer Inst. 79:1163–1172; Singh, et al. (1989) Biol. Chem. 264:3089–3095; Srinivasan, et al. (1985) *FEBS Letters* 192:113; Schwartz, et al. (1987) Endocrinology 121:1454–1460). Toxic moieties thus far investigated with these delivery agents include radionuclides (Ghose, et al. (1967) Br. Med. J. 1:90–96), cytotoxic drugs commonly employed in cancer chemotherapy (Thorp and Ross (1982) Immun. Rev, 62:119–157; Deweger, et al. (1982) Immun. Rev. 62:29–45; Arnon and Sela (1982) Immun. Rev. 62:5–27; Pimm, et al. (1982) Cancer Immun. Immunotherap, 12:125–134; Rowland and Axton (1985) Cancer Immun. Immunotherap. 19:1–7) and proteins derived from bacteria and plants such as diptheria or ricin (Jansen, et al. (1982) Immun. Rev. 62:185–216; Raso (1982) Immun. Rev. 62:93–117; Vitetta, et al. (1982) Immun. Rev. 62:159–183; Nelville and Youle (1982) Immun. Rev. 62:47–73; Thorpe, et al. (1981) Eur. J. Biochem. 116:447–454). A specific molecule is designed by replacing the nonspecific B chain with an antibody or a hormone.

Bacterial and plant toxins, such as diphtheria toxin (DT), Pseudomonas aeruginosa toxin A, abrin, ricin, mistletoe, modeccin, and Shigella toxin, are potent cytocidal agents due to their ability to disrupt a critical cellular function. For instance, DT and ricin inhibit cellular protein synthesis by inactivation of elongation factor-2 and inactivation of ribosomal 60s subunits, respectively (Bacterial Toxins and Cell Membranes, Eds. Jelajaszewicz and Wadstrom (1978) Academic Press, p. 291). These toxins are extremely potent because they are enzymes and act catalytically rather than stoichiometrically. The molecules of these toxins are composed of an enzymatically active polypeptide chain or fragment, commonly called "A" chain or fragment, linked to one or more polypeptide chains or fragments, commonly called "B" chains or fragments, that bind the molecule to the cell surface and enable the A chain to reach its site of action, e.g., the cytosol, and carry out its disruptive function. The act of gaining access to the cytosol is called variously "internalization", "intoxication", or "translocation". These protein toxins belong to a class bearing two chains referred to as A and B chains. The B chain has the ability to bind to almost all cells whereas the cytotoxic activity is exhibited by the A chain. It is believed that the A chain must be timely liberated from the B chain-frequently by reduction of a disulfide bond-in order to make the A chain functional. These natural toxins are generally not selective for a given cell or tissue type because their B chains recognize and bind to receptors that are present on a variety of cells.

The availability of a toxin molecule which is not cytotoxic to a variety of cells when administered alone has been limited. Utilizing certain naturally occurring single chain toxin molecules which do not themselves bind to cell surface receptors and, therefore, are not normally internalized by cells, has provided toxic molecules which are relatively non-toxic to most, if not all, cells when administered alone. Such naturally occurring single chain toxins known to date, include, but are not limited to, pokeweed antiviral protein (Ramakrishnan and Houston (1984) Cancer Res. 44:201–208), saponin (Thorpe, et al. (1985) J. Natl. Cancer Inst. 75:151–159), and gelonin (Stirpe, et al (1980) J. Biol. Chem. 255:6947–6953). These proteins are nontoxic to cells in the free form, but can inhibit protein synthesis once they gain entry into the cell. However, the availability of these single chain toxins in substantially pure form is limited due to the fact that they must be purified from plant sources in which they occur in relatively low amounts and the reproducibility of the concentration of the toxin in the plants is dependent upon plant growth conditions and plant harvest conditions.

Gelonin is a single chain polypeptide isolated from seeds of a plant, Gelonium multiforum, having a molecular weight of approximately 28,000–30,000 kd. Gelonin is a basic glycoprotein with an approximate isoelectric point of 8.15 and contains mannose and glucosamine residues (Falasca, et al. (1982) Biochem J, 207:505–509). In contrast to other plant and bacterial toxins, this protein is not toxic to cells by itself, but when delivered to cells through a carrier, it damages the 60s ribosomal subunit. In vivo and in vitro biological data suggest that gelonin is equivalent or superior to other plant toxins. In fact, the results of a comparison of gelonin conjugates in vitro and in vivo with other A chain conjugates indicated that gelonin had similar potency, better selectivity, better tumor localization, and more significant therapeutic effects (Sivan, et al (1987) Cancer Res. 47:3169–3173). However, the availability of a reproducible, readily accessible supply of gelonin from natural sources is limited. In addition, the purification of gelonin from plant sources is difficult and the yield is very low.

Gelonin by itself has been shown to be abortifacient in mice and enhances antibody dependent cell cytotoxicity (Yeung, et al (1988) Internatl. J. Peptide Protein Res. 31:265–268).

Several investigators have utilized gelonin as a cytotoxic agent chemically attached to monoclonal antibodies or to peptide hormone cellular targeting ligands. However, chemical modification of gelonin and cellular targeting moieties can reduce targeting efficiency and cytotoxic potential of gelonin itself. Furthermore, natural sources of gelonin are subject to variability in harvesting and plant growth which can affect gelonin cytotoxic activity. The ability to produce a synthetic gelonin toxin, chemically or utilizing recombinant technology, provides a plentiful, reproducible source of the toxin.

SUMMARY OF THE INVENTION

The present invention provides substantially pure gelonin having the amino acid sequence shown in FIG. 1. The present invention also provides the DNA sequence for gelonin shown in FIG. 2. Utilization of the sequences of the present invention to produce substantially pure gelonin in plentiful amounts by recombinant technology provides abundant amounts of the toxin which were not heretofore available from natural sources.

BRIEF DESCRIPTION OF THE DRAWINGS

FIG. 2 demonstrates the cDNA encoding for gelonin.

DETAILED DESCRIPTION OF THE INVENTION

The term "substantially pure" when applied to the gelonin protein of the present invention means that the polypeptide is essentially free of other plant proteins normally associated with the gelonin in its natural state and exhibiting reproducible electrophoretic or chromatographic response, elution profiles, and toxic activity. The term "substantially pure" is not meant to exclude artificial or synthetic mixtures of the gelonin protein with other compounds.

Gelonin was purified from the seeds of the plant Gelonium multiforum by techniques known to those of skill in the art. The amino acid sequence was determined utilizing a modification of the Edman degradation method.

Samples of gelonin were applied to the reverse phase reaction chamber and subjected to Edman degradation. The N-terminal of gelonin was found to be heterogeneous (½ of the molecules of the protein were apparently one amino acid shorter than the others). This heterogeneity made it difficult to sequence much more than 40 cycles. Therefore, in order to determine further amino acids in the sequence, enzymatic cleavage was performed.

Internal sequence of proteins is generally obtained by digesting or cutting up the large protein molecule into smaller pieces with a combination of enzymes and chemical cleavages. When native gelonin was exposed to various protolytic enzyzme digestions, it was found to be incompletely cleaved. This was found to be partly due to a disulfide bond in the N-terminal part of the molecule. Breaking of this bond by reduction and alkylation with iodoacetic acid yielded a fragment that was less soluble than the native material at the pH required for enzymatic digestion. A combination of digestion of native gelonin with trypsin, Lysine aminopeptidase (Lysc), staphylococcal protease (V8), and chymotrypsin yielded peptides mostly from the C-terminal portion of the molecule. This indicated that the N-terminal part of the molecule (from the N-terminal analysis to the Asp-Ala-Pro at residue 70) was not readily accessible by enzyme digestions.

Figure 4:
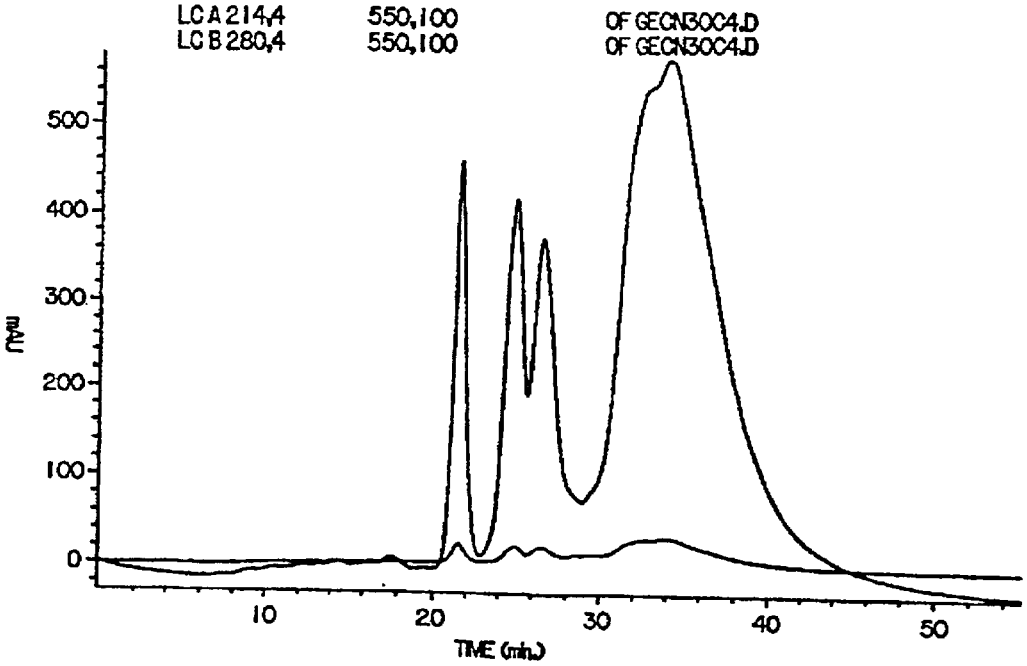
FIG. 4 demonstrates the HPLC profile of CNBr fragments.

Gelonin was cleaved with cyanogen bromide into 3 large peptides. Protein aliquots (0.2 mg/ml) were dissolved in 70% formic acid. A crystal of cyanogen bromide was added to the solution and the reaction allowed to proceed for at least 18 hours. The solution was then diluted with water and was applied to a small sequencing column. After sample application, a gradient of 1% to 10% n-propanol with 0.1% TFA was used to elute the protein fragments. The elution profile is shown on FIG. 4.

Enzymatic digestion of the whole protein or of CNBr fragments yeilded overlapping peptides. Enzymatic digestions with Lysyl endopeptidase in 0.1% SDS 100 mM Tris pH 8.0, Staphylococcus aureus protease in 0.1% SDS or trypsin in 0.1% Tween 20 were carried out. Gelonin contains one cysteine residue at position 49. Reduction and carboxymethylation yields a protein which recovers better on reverse phase HPLC and is more susceptible to enzymatic digestion. Therefore, most of the enzymatic digestions were carried out in 0.1% SDS or 0.1% Tween.

Figure 5A:
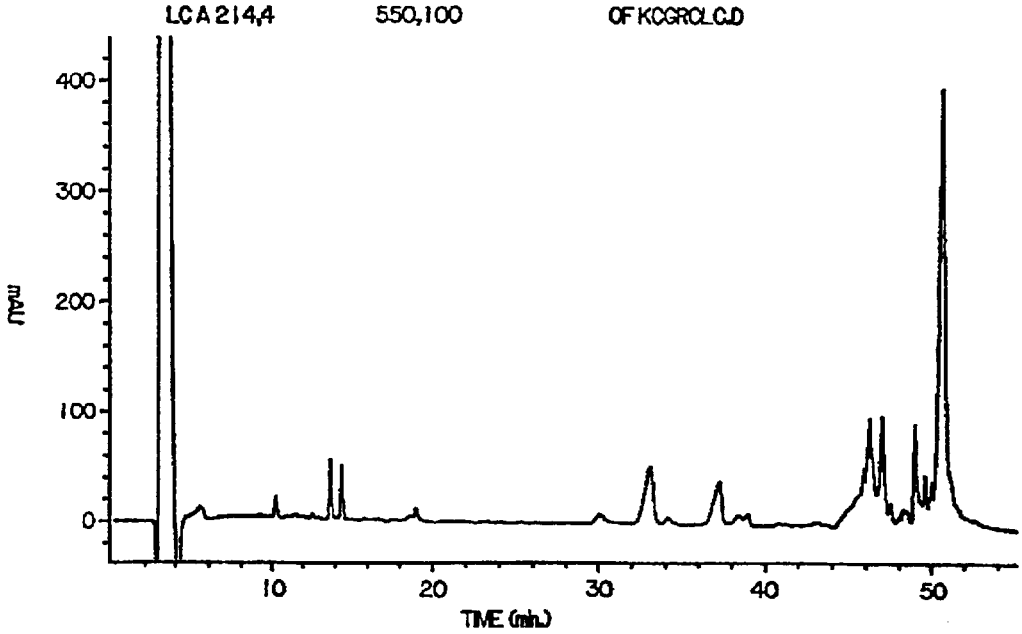
FIGS. 5A, 5B and 5C demonstrate the HPLC profile of (A) Lys-c, (B) Staphylococcus protease, and (C) Hydroxylamine digests of gelonin.
Figure 5B:
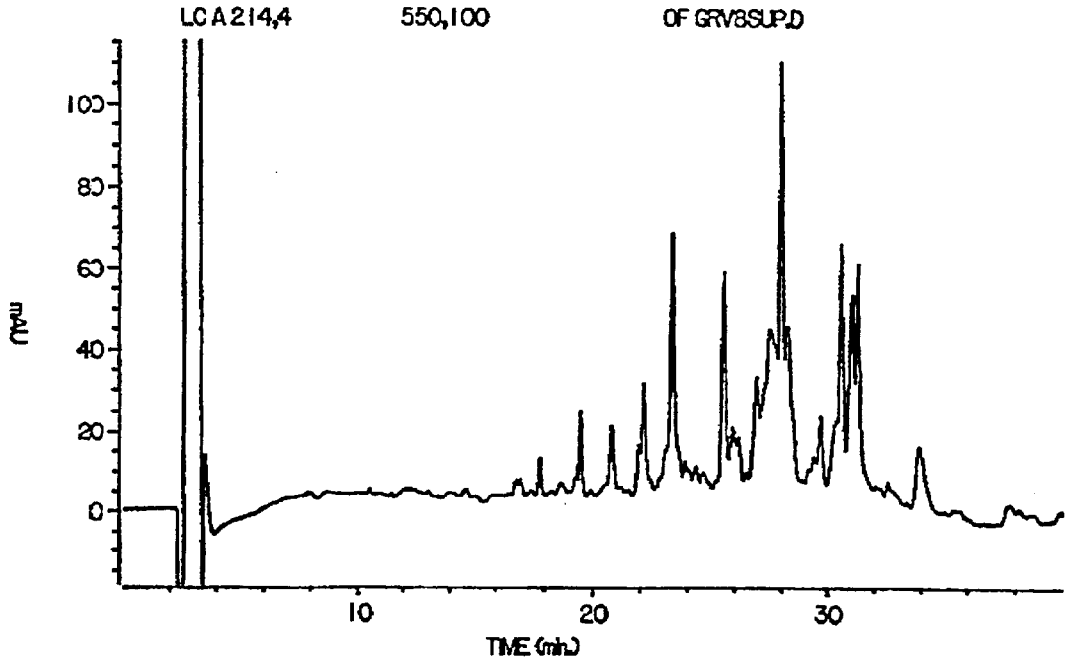

After the C-terminal 160 residues were aligned by a combination of CNBr digests and enzymatic cleavages, the remaining unknown sequence between residues 40 to 70 was determined by a combination of chemical modification of cysteine with iodoacetic acid and solubization of the alkylated protein with SDS. The RCM alkylated gelonin was then cleaved with excess Lysc enzyme at 37° C. for short periods of time (1–5 hr.). The HPLC elution profile is shown on FIG. 5A.

This method yielded a new sequence that had not been seen before. This new sequence showed the existence of an Asn-Gly combination. This combination of amino acids is cleaveable by a chemical method using hydroxylamine.

Figure 5C:
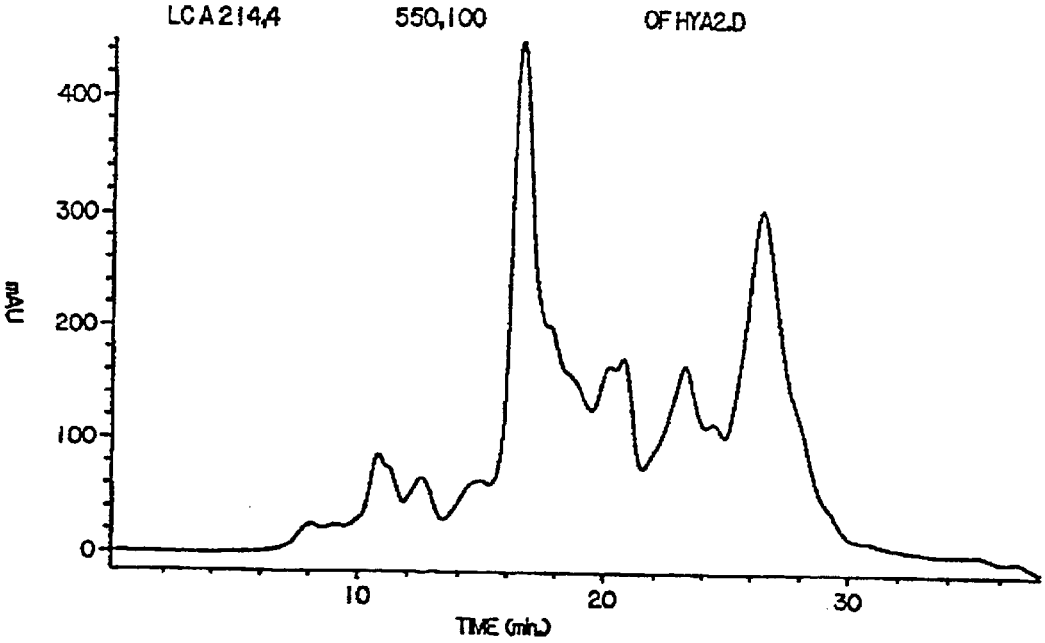
Figure 6A:
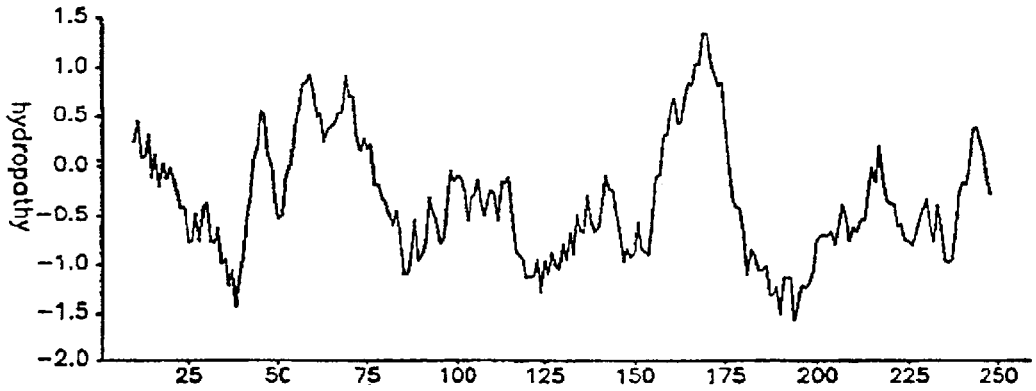
FIGS. 6A, 6B, 6C [and 6D], *6D and 6E* demonstrate the hydrophobicity plots of gelonin (A), trichosanthin (B), abrin (C), ricin (D), and agglutinin precursor (E).
Figure 6B:
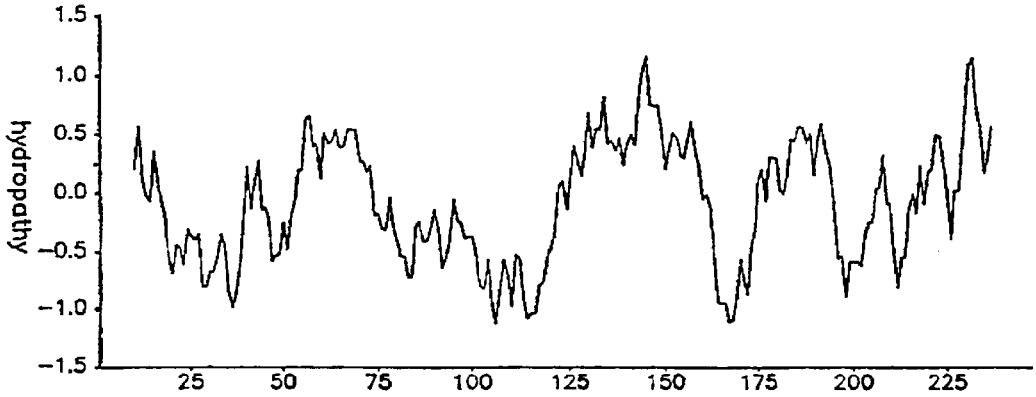
Figure 6C:
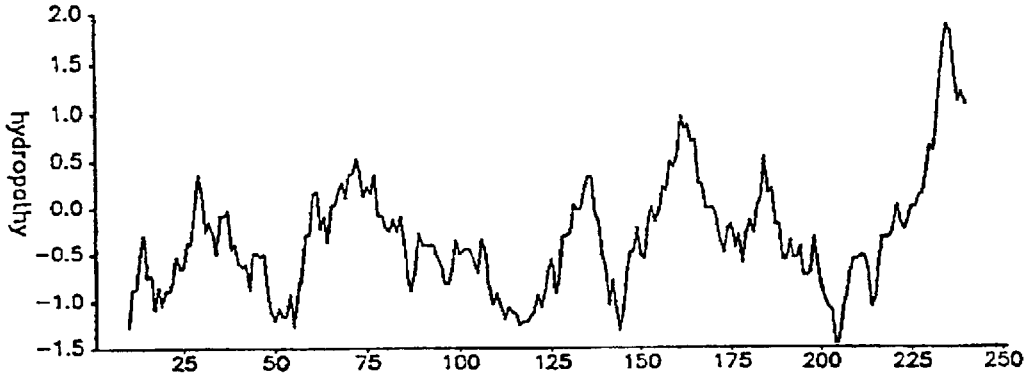
Figure 6D:
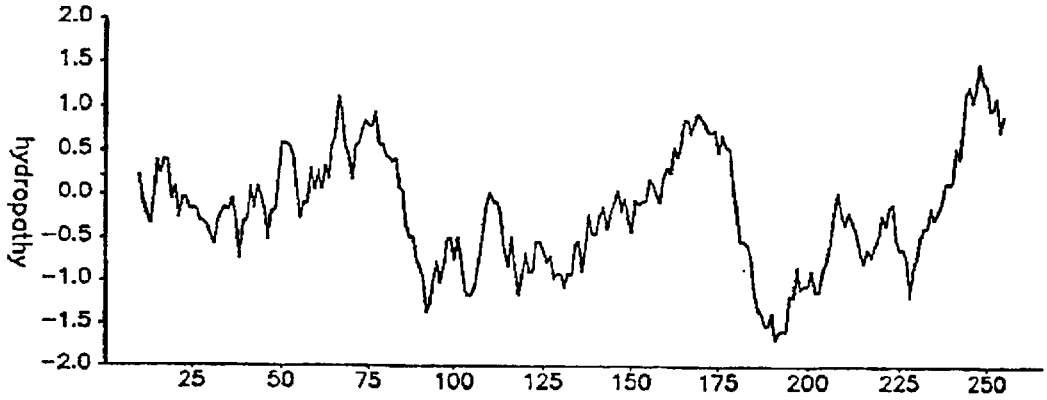
Figure 6E:
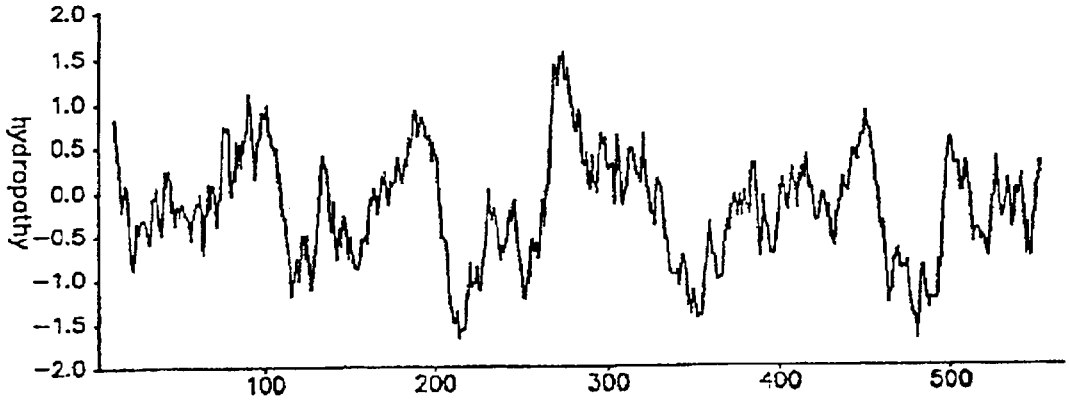

Hydroxylamine cleavage was carried out by adding 100 ug of gelonin to freshly prepared hydroxylamine (2M) in 0.2 M Tris (pH 9.0) with 2M NaCl, 1 mm EDTA and 10% ethanol. After incubation for 7 hours at room temperature, the entire reaction mixture was applied to a sequencing column. The column was then washed with 1% TFA in water and either eluted with an acetonitrile gradient or was sequenced directly as a mixture. This chemical cleavage produced a large hydrophobic peptide that contained about a 200 amino acid sequence which connected with the Asp-Ala-Pro at residue 70. The elution profile is shown on FIG. 5C.

The remaining, short section of overlapping sequence from between residues 40 to 50 was determined by digesting gelonin without alkylation by Lysc in SDS. This digested away most of the C-terminal part of the material. Then this mixture was digested again by chymotrypsin. The products of this digestion were then separated by HPLC. Sequence analysis of a large peptide revealed a sequence (SerThrLys) starting about 5 amino acids in from the N terminal end of the molecule. This was useful in that it removed the heterogeneous part of the molecule and allowed for a longer sequence run.

Figure 1:
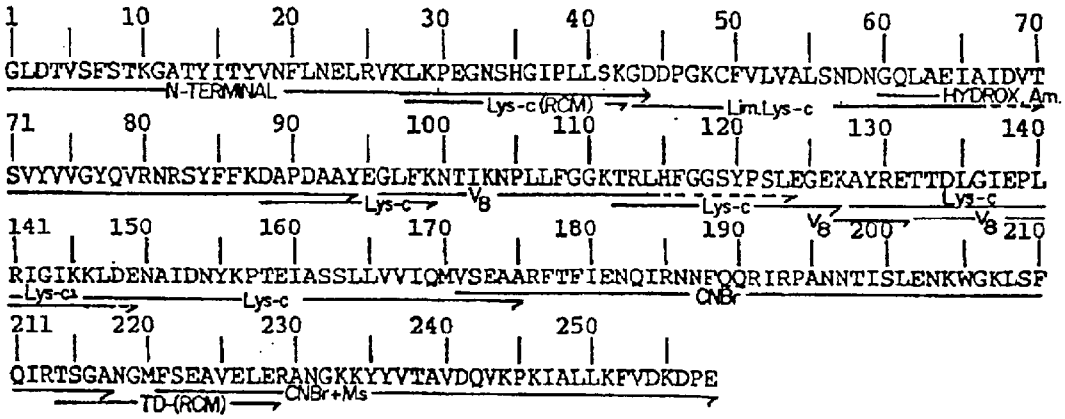
FIG. 1 shows the amino acid sequence of gelonin.
Figure 3:
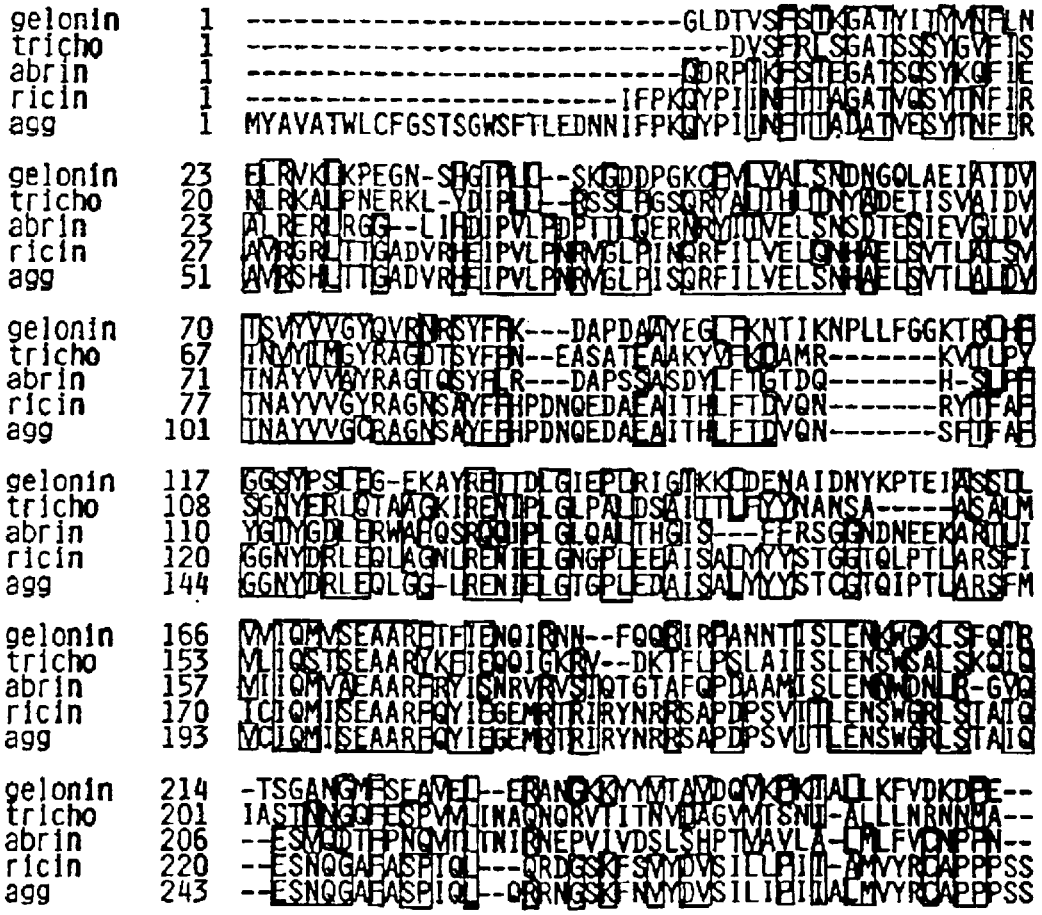
FIG. 3 demonstrates the homology of the gelonin amino acid sequence with the sequence of trichosanthin, Ricin A chain, Agglutinin precursor isolated from Castor bean and Abrin A chain.

Gelonin protein comprises 258 amino acids, the sequence of which is demonstrated on FIG. 1. The amino acid sequence of gelonin was compared to other known sequences available in sequence data banks (Genbank, PIR, EMBL) to determine whether gelonin has any areas of homology with other proteins. Comparison of the gelonin amino acid sequence with other proteins having known amino acid sequences demonstrated that the gelonin sequence is unique. Homology of certain portions of the gelonin sequence to portions of other proteins was detected. For instance, gelonin demonstrates a 36.0% homology with alphatrichosanthin from Trichosanthin kirilowi, 33.8% homology with Abrin A chain from Indian Liquorice, 35.2% homology with agglutinin precursor from Castor bean, 33.7% homology with Ricin D, A chain from Castor bean and 27.3% homology with antiviral protein (MAP) from Mirabills jalapa. A summary of the degree of homology to these and other proteins is shown on FIG. 3.

Hydrophobicity plots shown on FIGS. 6A–6E demonstrate a similarity to hydrophobic regions of trichosanthin, Ricin and to other ribosomal inhibiting proteins.

A plot of the hydropathy of the gelonin structure shows a hydrophobic region in residues 35–80 and 150–180. These are areas in which substantial folding of the molecule probably occurs. This similar hydrophobic pattern is also observed for other toxins (see FIGS. 6A–6E) and may suggest that the active enzymatic center may be contained within these folded regions. Therefore, the active enzymatic site may not be found in a linear region of the molecule and these structures may need to be adequately folded to attain the proper enzymatic center.

Utilizing the cDNA of gelonin, recombinant gelonin can be produced. Mutations can be specifically introduced into the molecule in order to provide recombinant gelonin lacking carbohydrate groups which can misdirect gelonin-antibody conjugates. Recombinant gelonin molecules can be produced by site directed mutagenesis to have greater toxic activity than the native molecule, to be more effectively internalized once bound to the cell surface by a carrier such as a monoclonal antibody or a targeting ligand such as IL-2, EGF, IFN, etc., to resist lysosomal degradation and thus be more stable and longer acting as a toxic moiety.

Recombinant gelonin molecules can also be engineered as fusion products to contain other functional modalities to kill cells such as an enzymatic activity, TNF, IFN activity, a second toxic activity, such as diptheria toxin action (wherein said second activity was through a different biological pathway than gelonin), thus creating a "supertoxin" or a toxin with multifunctional actions.

Fusion proteins can be engineered with gelonin to carry drugs such as chemotherapeutic agents or isotopes for radioimaging or radiotherapy. Gelonin peptides may have application as abortofacient agents, immuno suppressive agents, anticancer agents and as antiviral agents (such as an anti-HIV agent).

The following examples provide a detailed description of the preparation, characterization, and amino acid sequence of gelonin. The experimental methods utilized are described in detail in the examples below. These examples are not intended to limit the invention in any manner.

EXAMPLE 1

Purification and Characterization of Gelonin

Gelonin was isolated from the seeds of the plant Gelonium multiforum essentially according to the procedure as described (Stirpe, et al. (1980) J. Biol. Chem 255 6947–6953). Briefly, gelonin was extracted from the seeds by homogenization in buffered saline solution (pH 7.4). The supernatant was concentrated after dialysis against 5 mM sodium phosphate (pH 6.5) and the gelonin further purified by ion exchange chromatography as described below. The purity of the gelonin toxin was assessed by high pressure liquid chromatography (HPLC) and sodium dodecylsulphate-polyacylamide gel electrophoreseis (SDS-Page). Gelonin toxin migrated as a single band with an approximate molecular weight of 29–30,000 daltons.

Gelonin toxin activity was measured as described in Example 2 by protein synthesis inhibition in a cell-free system.

Seeds of Gelonium multiforum were shelled and the nuts ground in a homogenizer with eight volumes of 0.14 M NaCl containing 5 mM sodium phosphate (pH 7.4). The homogenate was left overnight at 4° C. with continuous stirring, cooled on ice and centrifuged at 35,000 times g for 20 minutes at 0° C. The supernatant was removed, dialyzed against 5 mM sodium phosphate (pH 6.5) and concentrated using a pm10 filter. The sample was layered on a CM-52 ion-exchange column (20×1.5 cm) equilibrated with 5 mM sodium phosphate (pH 6.5). Material which bound to the ion exchange resin was eluted with 400 ml of 0 to 0.3 M linear NaCl gradient at a rate of 25 ml hour at 4° C. Five ml fractions were collected. The fractions were monitored at 280 nm in a spectrophotometer. The gelonin eluted in about fractions 55–70 and was the last major elution peak. These fractions were pooled, dialyzed against 0.1 M NaCl in 0.1 M $Na_2HPO_4$ buffer (pH 7.4). The sample was then applied to a Cibacron blue sepharose column (24×2 cm) previously equilibrated with 0.1 M $Na_2HPO_4$/0.1 M NaCl buffer. The column was washed with 3 column volumes of buffer and eluted with a 400 ml linear salt gradient (from 0.1 M NaCl to 2 M NaCl). Elution of the bound material was monitored by Lowry assay of the column fractions. The fractions containing the single protein peak were pooled and dialyzed overnight at 4° C. against PBS. Gelonin toxin was purified to greater than 97% purity as estimated from silver stained PAGE. The purity and the molecular weight of each preparation was checked on high pressure liquid chromatography using a TSK 3000 gel permeation column with 50 mM sodium phosphate buffer, pH 7.4 and 15% sodium dodecylsulphate-polyacrylamide gel electrophoresis (SDS-page). Gelonin migrated as a single band with an approximate molecular weight of 29–30,000 daltons.

EXAMPLE 2

Assay of Gelonin Activity

The gelonin activity was monitored in a cell-free protein synthesis inhibition assay. The cell-free protein synthesis inhibition assay was performed by sequentially adding to 50 ul rabbit reticulocyte lysate, thawed immediately before use, mixing after each addition, the following components: 0.5 ml of 0.2 M Tris HCl (pH 7.8), 8.9 ml of ethylene glycol, and 0.25 ml of 1 M HCl).

Twenty microliters of a salt-amino acid-energy mixture (SAEM) consisting of: 0.375 M KCl, 10 mM $Mg(CH_3CO_2)_2$, 15 mM glucose, 0.25–10 mM amino acids (excluding leucine), 5 mM ATP, 1 mM GTP, 50 mM Tris-HCl (pH 7.6), 10 ul Creatinine phosphate-creatinine phosphokinase, 8 ul [$^{14}$C] leucine (Amersham, 348 mCi/mmol), and adding 1.5 ul of solutions containing varying concentrations of the gelonin mixture. The mixture was incubated for 60 minutes at 30° C. $^{14}$C-leucine incorporation was monitored in an aliquot of the mixture by precipitating synthesized protein on glass fiber filters, washing in 10% TCA and acetone, and monitoring the radioactivity in a Beta-counter using Aquasol scintillation fluid. Utilizing this assay, purified gelonin had a specific activity of $4\times10^9$ U/mg protein. A unit of gelonin activity is the amount of gelonin protein which causes 50% inhibition of incorporation of [$^{14}$C] leucine into protein in the cell free assay.

EXAMPLE 3

Determination of Gelonin Amino Acid Sequence

The gelonin amino acid sequence was determined by the Edman degradation method using an automated amino acid sequencer as described in European Patent Application No. EP-257735. Large peptides and unfragmented protein were applied to the reverse phase portion of the sequence reaction chamber. Unwanted buffer components were washed off with excess water. The protein or peptide sample was then sequenced by Edman chemistry and the extracted ATZ amino acid derivatives were converted to the PTH form by 25% TFA in $H_2O$ at 65° C. PTH samples were identified by reverse phase analytical separation on a Np 1090 column.

In order to obtain further amino acid sequence, the protein was digested with various proteolytic and chemical agents and then the peptides were purified by high performance liquid chromatography. Gelonin was found quite resistant to the exposure of trypsin (cleaves after arginine and lysine residues) and acetyl trypsin (cleaves only after lysine residue). The protein was found resistant to as much as 5% (w/w) of the enzyme. The resistance of gelonin to the proteolytic enzyme trypsin is not due to a lack of trypsin cleavage sites, since gelonin contains 21 lysine and 12 arginine residues. These results indicate that gelonin is perhaps a rigidly packed molecule which makes it inaccessible to proteolytic enzymes.

Since gelonin was found resistant to cleavage by proteolytic enzymes, chemical cleavage of the protein was examined.

EXAMPLE 4

CNBr Cleavage of Gelonin

Gelonin prepared as in Example 1 was dissolved in 70% formic acid. A crystal of cyanogen bromide was added to the solution. After at least 18 hours the solution was applied to either a small column (0.15 cm×5 cm) reverse phase (J. T. Baker, 15 cm C-1B bonded phase Cat II 7191-02) or analytical (4.6×100 mm) reverse phase column. A gradient elution of 1 to 70% n propanol with 1% TFA in water produced 5 peaks as shown on FIG. 6. Each of the peaks were sequenced and also used for further digestion by enzymes to piece together the entire sequence. Peak 1 was sequenced directly and gave a sequence starting with a Phe (F) that ran for 38 residues and ending with a Glu (E). This sequence was confirmed by mass spectroscopy and Lysc digestions of this isolated peptide. Peak 2 was sequenced directly and gave a sequence starting with a Val (V) that ran for 47 cy and was not interruptible after the Ala at cy 47. Peak 3 was sequenced and gave the same sequence as peak 2. SDS gels of peaks 2 and 3 as well as Lysc digestion of peaks 2 and 3 showed that peak 3 contained the C-terminal CNBr peptide as well. Subsequent trypsin digestion of gelonin produced a peptide that connected these two CNBr peptide sequences. This trypsin peptide when sequenced gave the sequence TSGANGMFSEAVELER. Peak 4 and 5 both gave the N-terminal sequence GLDT . . . . This was used for some digestion by Lysc, ⅛, to give peptides from its C-terminal end.

EXAMPLE 5

Enzymatic Digestion of CNBr Cleaved Gelonin

Samples of whole protein or CNBr fragments were digested with Lysyl endopeptidase (Wako Chemical Dallas, Tex.) in 0.1% SDS 100 mM Tris pH 8.0 or Staphylococcus aureus protease (Pierce) in 0.1% SDS or Trypsin (Sigma) in 0.1% Tween 20. Digestion mixtures were separated by HPLC and collected peptides were sequenced on the prototype sequence using gas-phase Edman sequencing methods.

EXAMPLE 6

Amino Acid Sequence of Gelonin

A total of 258 amino acid residue sequences were obtained following analysis of the CNBr fragments obtained in Example 3. FIG. 1 shows the amino acid sequence of gelonin. Gelonin contains a total of approximately 258 amino acid residues. The DNA sequence was deduced from this amino acid sequence. The degenerate DNA sequence is shown on FIG. 2. Those skilled in the art will recognize that fragments and derivatives of either the gelonin amino acid sequence or the DNA sequence coding for gelonin may inhibit cellular protein synthesis but not bind to a cell surface receptor.

The invention now being fully described, it will be apparent to one of ordinary skill in the art that many changes and modifications can be made thereto without departing from the spirit or scope of the invention as set forth below.

What is claimed as new and is desired to be covered under Letters Patent is:

1. Substantially pure gelonin toxin having the amino acid sequence:

```
GlyLeuAspThrValSerPheSerThrLys          10
GlyAlaThrTyrIleThrTyrValAsnPhe          20
LeuAsnGluLeuArgValLysLeuLysPro          30
GluGlyAsnSerHisGlyIleProLeuLeu          40
ArgLysGlyAspAspProGlyLysCysPhe          50
ValLeuValAlaLeuSerAsnAspAsnGly          60
GlnLeuAlaGluIleAlaIleAspValThr          70
SerValTyrValValGlyTyrGlnValArg          80
AsnArgSerTyrPhePheLysAspAlaPro          90
AspAlaAlaTyrGluGlyLeuPheLysAsn         100
ThrIleLysAsnProLeuLeuPheGlyGly         110
LysThrArgLeuHisPheGlyGlySerTyr         120
ProSerLeuGluGlyGluLysAlaTyrArg         130
GluThrThrAspLeuGlyIleGluProLeu         140
ArgIleGlyIleLysLysLeuAspGluAsn         150
AlaIleAspAsnTyrLysProThrGluIle         160
AlaSerSerLeuLeuValValIleGlnMet         170
ValSerGluAlaAlaArgPheThrPheIle         180
GluAsnGlnIleArgAsnAsnPheGlnGln         190
ArgIleArgProAlaAsnAsnThrIleSer         200
LeuGlnAsnLysTrpGlyLysLeuSerPhe         210
GlnIleArgThrSerGlyAlaAsnGlyMet         220
PheSerGluAlaValGluLeuGluArgAla         230
AsnGlyLysLysTyrTyrValThrAlaVal         240
AspGlnValLysProLysIleAlaLeuLeu         250
LysPheValAspLysAspProGlu               260
```

or a fragment or derivative thereof, said fragment or derivative having an activity which inhibits cellular protein synthesis but does not bind to a cell surface receptor.

2. A DNA sequence of the formula:

```
GGNYTNGAYA CNGTNWSNTT YWSNACNAAR GGNGCNACNT AYATHACNTA YGTNAAYTTY   60
YTNAAYGARY TNMGNGTNAA RYTNAARCCN GARGGNAAYW SNCAYGGNAT HCCNYTNYTN  120
MGNAARGGNG AYGAYCCNGG NAARTGYTTY GTNYTNGTNG CNYTNWSNAA YGAYAAYGGN  180
CARYTNGCNG ARATHGCNAT HGAYGTNACN WSNGTNTAYG TNGTNGGNTA YCARGTNMGN  240
AAYMGNWSNT AYTTYTTYAA RGAYGCNCCN GAYGCNGCNT AYGARGGNYT NTTYAATAAY  300
ACNATHAARA AYCCNYTNYT NTTYGGNGGN AARACNMGNY TNCAYTTYGG NGGNWSNTAY  360
CCNWSNYTNG ARGGNGARAA RGCNTAYMGN GARACNACNG AYYTNGGNAT HGARCCNYTN  420
MGNATHGGNA THAATAARYT NGAYGARAAY GCNATHGAYA AYTAYAARCC NACNGARATH  480
GCNWSNWSNY TNYTNGTNGT NATHCARATG GTNWSNGARG CNGCNMGNTT YACNTTYATH  540
GARAAYCARA THMGNAAYAA YTTYCARCAR MGNATHMGNC CNGCNAAYAA YACNATHWSN  600
YTNGARAAYA ARTGGGGNAA RYTNWSNTTY CARATHMGNA CNWSNGGNGC NAAYGGNATG  660
TTYWSNGARG CNGTNGARYT NGARMGNGCN AAYGGNAARA ARTAYTAYGT NACNGCNGTN  720
GAYCARGTNA ARCCNAARAT HGCNYTNYTN AARTTYGTNG AYAARGAYCC NGAR        774
wherein   R = A or G       K = G or T       N = any
          Y = C or T       M = A or C       S = C or G
          B = C, G, or T   V = A, C, or G   W = A or T
          D = A, G, or T   H = A, C, or T   X = unknown
```

or a fragment or derivative thereof, said fragment or derivative coding for gelonin or for a polypeptide having an activity which inhibits cellular protein synthesis but does not bind to a cell surface receptor.

*3. The toxin of claim 1 further defined as having the amino acid sequence:*

```
GlyLeuAspThrValSerPheSerThrLys
GlyAlaThrTyrIleThrTyrValAsnPhe
LeuAsnGluLeuArgValLysLeuLysPro
GluGlyAsnSerHisGlyIleProLeuLeu
ArgLysGlyAspAspProGlyLysCysPhe
ValLeuValAlaLeuSerAsnAspAsnGly
GlnLeuAlaGluIleAlaIleAspValThr
SerValTyrValValGlyTyrGlnValArg
AsnArgSerTyrPhePheLysAspAlaPro
AspAlaAlaTyrGluGlyLeuPheLysAsn
ThrIleLysAsnProLeuLeuPheGlyGly
LysThrArgLeuHisPheGlyGlySerTyr
ProSerLeuGluGlyGluLysAlaTyrArg
```

-continued

```
GluThrThrAspLeuGlyIleGluProLeu
ArgIleGlyIleLysLysLeuAspGluAsn
AlaIleAspAsnTyrLysProThrGluIle
AlaSerSerLeuLeuValValIleGlnMet
ValSerGluAlaAlaArgPheThrPheIle
GluAsnGlnIleArgAsnAsnPheGlnGln
ArgIleArgProAlaAsnAsnThrIleSer
LeuGluAsnLysTrpGlyLysLeuSerPhe
GlnIleArgThrSerGlyAlaAsnGlyMet
PheSerGluAlaValGluLeuGluArgAla
AsnGlyLysLysTyrTyrValThrAlaVal
AspGlnValLysProLysIleAlaLeuLeu
LysPheValAspLysAspProGlu.
```

*4. The DNA sequence of claim 2, further defined as having the nucleotide sequence:*

```
GGNYTNGAYA CNGTNWSNTT YWSNACNAAR GGNGCNACNT AYATHACNTA YGTNAAYTTY   60
YTNAAYGARY TNMGNGTNAA RYTNAARCCN GARGGNAAYW SNCAYGGNAT HCCNYTNYTN  120
MGNAARGGNG AYGAYCCNGG NAARTGYTTY GTNYTNGTNG CNYTNWSNAA YGAYAAYGGN  180
CARYTNGCNG ARATHGCNAT HGAYGTNACN WSNGTNTAYG TNGTNGGNTA YCARGTNMGN  240
```

-continued

```
AAYMGNWSNT AYTTYTTYAA RGAYGCNCCN GAYGCNGCNT AYGARGGNYT NTTYAATAAY  300

ACNATHAARA AYCCNYTNYT NTTYGGNGGN AARACNMGNY TNCAYTTYGG NGGNWANTAY  360

CCNWSNYTNG ARGGNGARAA RGCNTAYMGN GARACNACNG AYYTNGGNAT HGARCCNYTN  420

MGNATHGGNA THAARAARYT NGAYGARAAY GCNATHGAYA AYTAYAARCC NACNGARATH  480

GCNWSNWSNY TNYTNGTNGT NATHCARATG GTNWSNGARG CNGCNMGNTT YACNTTYATH  540

GARAAYCARA THMGNAAYAA YTTYCARCAR MGNATHMGNC CNGCNAAYAA YACNATHWSN  600

YTNGARAAYA ARTGGGGNAA RYTNWSNTTY CARATHMGNA CNWSNGGNGC NAAYGGNATG  660

TTYWSNGARG CNGTNGARYT NGARMGNGCN AAYGGNAARA ARTAYTAYGT NACNGCNGTN  720

GAYCARGTNA ARCCNAARAT HGCNYTNYTN AARTTYGTNG AYAARGAYCC NGAR        774
wherein   R = or G         K = G or T       N = any
          Y = C or T       M = A or C       S = C or G
          B = C, G, or T   V = A, C, or G   W = A or T
          D = A, G, or T   H = A, C, or T   X = unknown.
```

*5. The gelonin toxin of claim 1 or claim 3, further defined as a fusion protein that includes a functional modality in addition to said toxin.*

*6. The gelonin toxin of claim 5 wherein the fusion protein is prepared by conjugation of the functional modality to the toxin.*

*7. The gelonin toxin of claim 5, wherein the fusion protein is prepared by recombinant technology.*

*8. The gelonin toxin of claim 5, wherein said functional modality is an antibody.*

*9. The gelonin toxin of claim 5, wherein the functional modality is a targeting ligand.*

*10. The gelonin toxin of claim 9, wherein the targeting ligand is IL-2.*

*11. The gelonin toxin of claim 9, wherein the targeting ligand is EGF.*

*12. The gelonin toxin of claim 9, wherein the targeting ligand is IFN.*

*13. The gelonin toxin of claim 5, wherein the functional modality is a second toxic activity.*

*14. The gelonin toxin of claim 13, wherein said second toxic activity is diptheria toxin action.*

*15. The gelonin toxin of claim 5 wherein the functional modality is TNF.*

*16. The gelonin toxin of claim 5, wherein the functional modality is a chemotherapeutic agent.*

*17. The gelonin toxin of claim 5, wherein the functional modality is a radioisotope.*

*18. The gelonin toxin of claim 1 or claim 3, further defined as lacking carbohydrate groups.*

* * * * *

UNITED STATES PATENT AND TRADEMARK OFFICE

CERTIFICATE OF CORRECTION

PATENT NO. : RE 37,462 E 
DATED : December 4, 2001
INVENTOR(S) : Michael Rosenblum, William J. Kohr and Bharat Aggarwal It is certified that error appears in the above-identified patent and that said Letters Patent is hereby corrected as shown below:

Column 9,
Claim 2, please delete amino acid residue no. 435 "T" and insert -- R -- therefor.

Column 11,
Claim 4, please delete amino acid residue no. 297 "T" and insert -- R -- therefor.
Claim 4, please delete amino acid residue no. 356 "A" and insert -- S -- therefor.
Claim 4, please delete "R= or G" and insert -- R= A+G -- therefor.

Signed and Sealed this

Second Day of September, 2003

JAMES E. ROGAN
*Director of the United States Patent and Trademark Office*